(12) United States Patent
Groβe Böwing et al.

(10) Patent No.: US 8,507,712 B2
(45) Date of Patent: Aug. 13, 2013

(54) METHOD FOR PRODUCING DIPHENYLCARBONATE HAVING CATALYST COMPRISING IONIC FLUIDS

(75) Inventors: Alexandra Groβe Böwing, Dormagen (DE); Aurel Wolf, Wülfrath (DE); Kilian Tellmann, Frankfurt am Main (DE); Leslaw Mleczko, Dormagen (DE)

(73) Assignee: Bayer Technology Services GmbH, Leverkusen (DE)

( * ) Notice: Subject to any disclaimer, the term of this patent is extended or adjusted under 35 U.S.C. 154(b) by 209 days.

(21) Appl. No.: 13/120,086

(22) PCT Filed: Sep. 17, 2009

(86) PCT No.: PCT/EP2009/006721
§ 371 (c)(1),
(2), (4) Date: Mar. 21, 2011

(87) PCT Pub. No.: WO2010/037477
PCT Pub. Date: Apr. 8, 2010

(65) Prior Publication Data
US 2011/0172454 A1    Jul. 14, 2011

(30) Foreign Application Priority Data
Sep. 30, 2008  (DE) .......................... 10 2008 049 787

(51) Int. Cl.
*C07C 69/96* (2006.01)
*B01J 31/12* (2006.01)
*C07F 15/00* (2006.01)

(52) U.S. Cl.
USPC ........... 558/274; 502/164; 502/167; 548/101; 548/402

(58) Field of Classification Search
USPC ................ 558/274; 502/164, 167; 548/101, 548/402
See application file for complete search history.

(56) References Cited

U.S. PATENT DOCUMENTS

| 5,712,406 A | 1/1998 | Buysch |
| 2004/0192953 A1 | 9/2004 | Reisinger et al. |

FOREIGN PATENT DOCUMENTS

| EP | 1 460 055 A1 | 9/2004 |
| JP | 2003 146933 A1 | 5/2003 |
| JP | 2004 050142 A | 2/2004 |
| JP | 2007 039387 A | 2/2007 |
| WO | 03/055603 A1 | 7/2003 |
| WO | 2006/088348 A1 | 8/2006 |

OTHER PUBLICATIONS

Hallgren, et al., "The Palladium-Catalyzed Synthesis of Diphenyl Carbonate From Phenol Carbon Monoxide, and Oxygen", Journal of Organometallic Chemistry, vol. 204, pp. 135-135, Jan. 1981.
Xin, B. "Phosphine-Free Cross-coupling Reaction of Halopyridines with Arylboronic Acids in an Ionic Liquid : water Mixtures", Journal of Chemical Research, No. 7, pp. 412-415, Jul. 1, 2008.
Vallette, et al., "Palladium Catalyzed C-P Cross-Coupling Reactions in Ionic Liquids", Tetrahedron Letters, Elsvier, vol. 47, No. 29, pp. 5191-5193, Jul. 17, 2006.
International Search Report Dated Nov. 27, 2009.

*Primary Examiner* — Joseph Kosack
(74) *Attorney, Agent, or Firm* — Norris McLaughlin & Marcus PA

(57) ABSTRACT

The invention relates to a method for producing diphenylcarbonate while using a catalyst composition comprising ionic fluids.

11 Claims, 1 Drawing Sheet

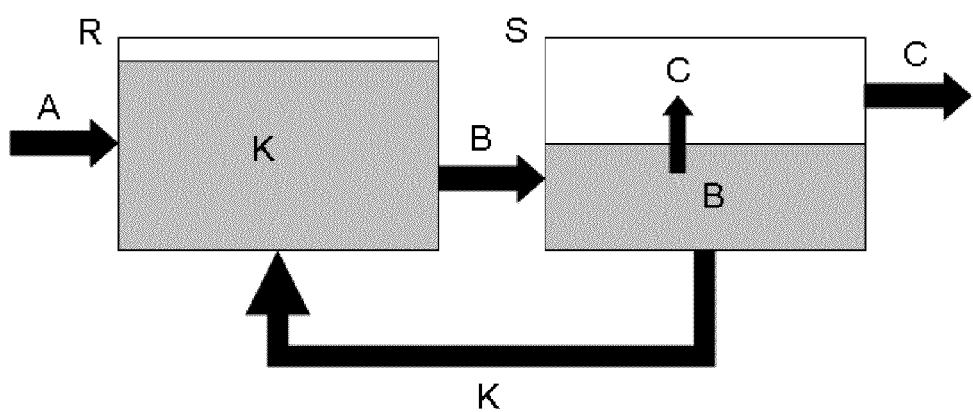

METHOD FOR PRODUCING DIPHENYLCARBONATE HAVING CATALYST COMPRISING IONIC FLUIDS This is a 371 of PCT/EP2009/006721, filed 17 Sep. 2009 (international filing date), which claims foreign priority benefit under 35 U.S.C. §119 of German Patent Application No. 10 2008 049 787.8, filed Sep. 30, 2008

BACKGROUND OF THE INVENTION

The invention relates to a method for producing diphenylcarbonate while using a catalyst composition comprising ionic fluids.

Diphenyl carbonates are intermediates in processes for preparing polycarbonates. Polycarbonates are in turn synthetic polymers from the family of polyesters.

At present, two general process routes are generally known for preparing polycarbonate.

In a first process variant, an aqueous solution or suspension of a bisphenol sodium salt is placed in a reaction vessel and gaseous phosgene is introduced in the presence of a solvent for polycarbonate. This results in a polycondensation reaction to form polycarbonate.

In a second process variant, bisphenol A, diphenyl carbonate and a transesterification catalyst are melted together. The major part of the phenol is then distilled off under reduced pressure and the pressure is then reduced further, with the polycondensation reaction to form polycarbonate commencing and the remaining phenol being given off from the now viscous melt.

The invention described here thus relates, in particular, to the preparation of diphenyl carbonate for further reaction to form polycarbonates according to the two process variants just described.

A generally known problem in processes for preparing diphenyl carbonate is that they are mainly homogeneously catalyzed processes, so that recovery of the catalyst from the reaction mixture is at least complicated, often even not economically feasible.

A further generally known problem in such processes for preparing diphenyl carbonate is that the generally known metal salts used in the catalyst compositions tend to form colloidal particles in the reaction composition, which particles then either precipitate from the homogeneous phase or deposit on the wall of the reaction apparatus. Although this alleviates the abovementioned problems of recovery, the metal salts are as a result no longer available in sufficient quantity to the reaction and/or their activity decreases significantly, so that the process is once again operated uneconomically.

WO 2006 088348 A1 discloses a process in which an ionic liquid and carbon dioxide are used as solvent mixture at a particular pressure and a particular temperature in such a way that the two solvents form a homogeneous phase with the reaction mixture at a first point in time and the pressure and the temperature are then changed at a later point in time so that a phase comprising the ionic liquid and a phase comprising the carbon dioxide are formed, with the latter being essentially free of ionic liquid.

The ionic liquid in WO 2006 088348 A1 can also comprise a catalyst or the ionic liquid is itself the catalyst. A characteristic of the process disclosed in WO 2006 088348 A1 is the necessary presence of carbon dioxide as solubilizer between reaction mixture and solvent mixture. The process disclosed is particularly suitable for reactions of organic material. Furthermore, it is disclosed that the catalyst compositions present in the ionic liquid preferably likewise have ionic character.

In WO 2006 088348 A1, it is not specifically disclosed that the ionic liquid is 1-butyl-3-methylpyrrolidinium trifluoroacetate or 1-butyl-3-methylimidazolium hexafluorophosphate or a mixture thereof. Furthermore, further catalyst compositions which may be present in the phase are not individually disclosed with the exception of phosphine-noble metal catalysts. Although WO 2006 088348 A1 specifically discloses 1-butyl-3-methylimidazolium tetrafluoroborate, a person skilled in the art will know that particularly in the class of ionic liquids even small changes in a constituent of the ionic liquid have a great influence on the properties thereof. Thus, the abovementioned 1-butyl-3-methylimidazolium tetrafluoroborate is hydrophilic, while 1-butyl-3-methylimidazolium hexafluorophosphate has hydrophobic character.

In particular, there is no disclosure of a catalyst composition containing a palladium salt, a manganese salt and a base in an ionic liquid. The process is not specifically disclosed for usability in the course of a carbonylation.

Proceeding from the prior art, it is thus an object of the invention to provide a catalyst composition which comprises ionic liquids and can be used, in particular, in carbonylations to produce diphenyl carbonate and allows such processes to be operated without complicated recovery of the catalyst composition and which has no tendency to form colloidal particles.

A further object is to provide a process for preparing diphenyl carbonate within which the desired diphenyl carbonate can be produced with high selectivity and in high yield in a simple and economically advantageous manner without the necessity of a complicated recovery of the catalyst composition and without a loss of activity of the metal salts.

SUMMARY OF THE INVENTION

It has now surprisingly been found, as first subject of the present invention, that a catalyst composition comprising an ionic liquid for preparing diphenyl carbonate, characterized in that the ionic liquid is 1-butyl-3-methylpyrrolidinium trifluoroacetate or 1-butyl-3-methylimidazolium hexafluorophosphate or a mixture thereof and in that the catalyst composition additionally contains a palladium salt, a manganese salt and a base, is able to achieve this object.

DETAILED DESCRIPTION

Preferred palladium salts are palladium bromide, palladium acetate and palladium chloride.

Preferred manganese salts are manganese(II) acetylacetonate, manganese(III) acetylacetonate, manganese(II) acetate, manganese(III) acetate and manganese bromide.

The palladium salts and manganese salts are also referred to collectively as metal salts for the purposes of the present invention.

In the context of the present invention, bases are materials having the general composition $A^{m+}(Y)^-_m$, where A is an atom of groups I and II and m is one of the natural numbers 1 and 2 or A is an ammonium ion and m is 1.

Y can be either OH or an organic group having the general composition R—O. Preference is given to R—O being an alkoxide group. R—O is particularly preferably an alkoxide group comprising at least one aromatic radical which is covalently bound thereto.

Particularly preferred bases are NaOH, KOH, sodium phenoxide and ammonium phenoxide.

In a preferred embodiment of the catalyst composition, the ionic liquid is 1-butyl-3-methylpyrrolidinium tetrafluoroacetate or 1-butyl-3-methylimidazolium hexyluorophosphate.

In a further preferred embodiment of the catalyst composition, the ionic liquid is 1-butyl-3-methylpyrrolidinium trifluoroacetate or 1-butyl-3-methylimidazolium hexyluorophosphate or a mixture thereof and the palladium salt is palladium bromide, the manganese salt is manganese(III) acetylacetonate and the base is sodium phenoxide.

Particular preference is given to the ionic liquid being 1-butyl-3-methylpyrrolidinium trifluoroacetate or 1-butyl-3-methylimidazolium hexyluorophosphate and the palladium salt being palladium bromide, the manganese salt being manganese(III) acetylacetonate and the base being sodium phenoxide.

The catalyst composition of the invention and its preferred embodiment are particularly advantageous since the ionic liquids selected surprisingly stabilize, in particular, palladium salts in the solution, so that the problems of formation of agglomerated, colloidal particles can be avoided in this way and a loss of the metal salt or a reduction in the activity for the reaction to be carried out no longer has to be feared.

Furthermore, the selected metal salts, in particular, in combination with the ionic liquids used according to the invention are particularly active in the carbonylation of phenol, so that the combination of the selected metal salts with the selected ionic liquids leads to particularly advantageous conversions in the process for preparing diphenyl carbonate from phenol.

A further advantage of the catalyst composition of the invention and its preferred embodiment is that owing to the ionic character of the palladium salt, the manganese salt and the base in combination with the ionic liquid, these have a high affinity with the ionic liquid, as a result of which these components are essentially present in immobilized form in the catalyst composition.

The catalyst composition of the invention and its preferred embodiments preferably contain from 0.01 to 0.06% by weight of palladium salt, from 0.1 to 0.5% by weight of manganese salt and from 0.5 to 6% by weight of base in the ionic liquid.

The lower limit to the proportion of the palladium salt and the manganese salt in the catalyst composition is advantageously very low due to the abovementioned positive effect of the combination with the ionic liquid since there is no need to fear a loss due to immobilization, which is economically advantageous. The upper limit is likewise advantageously low and imposed essentially by economic considerations since further metal salt would produce no significant improvement.

The catalyst of the invention can be obtained in a simple way by mixing the abovementioned constituents of the catalyst composition.

The invention further provides a process for preparing diphenyl carbonate from a reaction mixture comprising phenol, carbon monoxide and also oxygen and optionally diphenyl carbonate in a reaction zone, characterized in that the reaction mixture in the reaction zone is passed through a catalyst composition containing an ionic liquid which is 1-butyl-3-methylpyrrolidinium trifluoroacetate or 1-butyl-3-methylimidazolium hexafluorophosphate or a mixture thereof, a palladium salt, a manganese salt and a base.

The palladium salts which are preferably used in the process are those which have been disclosed above in connection with the catalyst composition of the invention.

Manganese salts and bases which are preferred and can be used are likewise those which have been disclosed above in connection with the catalyst composition of the invention.

In a preferred embodiment of the process of the invention, the ionic liquid is 1-butyl-3-methylpyrrolidinium trifluoroacetate or 1-butyl-3-methylimidazolium hexafluorophosphate.

In a further preferred embodiment of the process of the invention, the ionic liquid is 1-butyl-3-methylpyrrolidinium trifluoroacetate or 1-butyl-3-methylimidazolium hexafluorophosphate or a mixture thereof and the palladium salt is palladium bromide, the manganese salt is manganese(III) acetylacetonate and the base is sodium phenoxide.

Particular preference is given to the ionic liquid being 1-butyl-3-methylpyrrolidinium trifluoroacetate or 1-butyl-3-methylimidazolium hexafluorophosphate and the palladium salt being palladium bromide, the manganese salt being manganese(III) acetylacetonate and the base being sodium phenoxide.

The reaction mixture is preferably present in molecularly dissolved form in the catalyst composition in the reaction zone.

A temperature of from 75 to 150° C., preferably from 85 to 110° C., usually prevails in the reaction zone. Furthermore, a pressure of from 3 to 80 bar, preferably from 15 to 30 bar, usually prevails in the reaction zone.

The pressures and temperatures according to the invention in the reaction zone are particularly advantageous because a particularly high conversion of phenol and carbon monoxide and also oxygen into diphenyl carbonate can be obtained at these.

Furthermore, the combined reaction conditions in respect of pressure and temperature can be selected particularly advantageously since the ionic liquid, the palladium salt, the manganese salt and the base are present in solution in the catalyst composition and none of these materials has a significant vapor pressure under the reaction conditions indicated, so that the high conversion can be achieved without the risk of a loss of the catalyst composition as a result of vaporization, as would be the case in processes using homogeneous catalysis in a generally known solvent.

In a preferred further development of the process of the invention for preparing diphenyl carbonate, the reaction mixture is passed through a separation zone after the reaction zone.

The preferred further development of the process of the invention for preparing diphenyl carbonate is particularly advantageous because two phases are formed in the separation zone and the separate product phase can be separated off from the catalyst composition containing the ionic liquid, the palladium salt, the manganese salt and the base by simple phase separation. This allows simple and inexpensive separation of the reaction mixture from the catalyst composition and then essentially complete reuse of the catalyst composition.

The catalyst composition which has been surprisingly found according to the present invention is, according to the process disclosed here, preferably used in processes for preparing diphenyl carbonate.

The present invention therefore further provides for the use of a mixture containing 1-butyl-3-methylpyrrolidinium trifluoroacetate or 1-butyl-3-methylimidazolium hexafluorophosphate or a mixture thereof, a palladium salt, a manganese salt and a base for preparing diphenyl carbonate from a reaction mixture comprising phenol, carbon monoxide and oxygen.

Preference is given to using a mixture containing 1-butyl-3-methylpyrrolidinium trifluoroacetate or 1-butyl-3-methylimidazolium hexafluorophosphate or a mixture thereof, palladium bromide, manganese(III) acetylacetonate and sodium phenoxide.

Particular preference is given to using a mixture containing 1-butyl-3-methylpyrrolidinium trifluoroacetate or 1-butyl-3-methylimidazolium hexafluorophosphate, palladium bromide, manganese(III) acetylacetonate and sodium phenoxide.

The invention will be described below with the aid of examples and figures, without being restricted thereto.

BRIEF DESCRIPTION OF THE DRAWING

FIG. 1 shows an embodiment of the process of the invention, in which a reaction mixture (A) comprising phenol, carbon monoxide and oxygen is introduced into a reaction zone (R) containing the catalyst composition (K) at a pressure $p_1$. The reaction takes place in this reaction zone and a reaction mixture (B) comprising phenol, carbon monoxide and oxygen, diphenyl carbonate and the catalyst composition is obtained. The reaction mixture (B) is then introduced into a separation zone (S) in which a reaction mixture (C) comprising phenol, carbon monoxide and oxygen and diphenyl carbonate settles out as a separate phase from the catalyst composition (K). The catalyst composition (K) is recirculated to the reaction zone (R).

EXAMPLES

Example 1

Catalyst Composition According to the Invention

A first catalyst composition according to the invention consisting of 0.19 g of $PdBr_2$, 1.9 g of manganese(III) acetylacetonate, 1.8 g of sodium phenoxide and 3.0 g of 1-butyl-3-methylpyrrolidinium trifluoroacetate (Fluka) and 9 g of molecular sieves 3A (pore size: 3 Ångström; Fluka) was obtained by weighing the individual constituents into a glass beaker.

Example 2

Catalyst Composition According to the Invention

A second catalyst composition according to the invention identical to that of Example 1 except that 3.0 g of 1-butyl-3-methylimidazolium hexafluorophosphate (Fluka) were weighed out instead of 3.0 g of 1-butyl-3-methylpyrrolidinium trifluoroacetate was obtained by weighing the individual constituents into a glass beaker.

Example 3

Catalyst Composition According to the Invention

A third catalyst composition according to the invention consisting of 0.019 g of $PdBr_2$, 0.19 g of manganese(III) acetylacetonate, 0.18 g of sodium phenoxide and a mixture of 0.15 g of 1-butyl-3-methylpyrrolidinium tetrafluoroacetate (Fluka) and 0.15 g of 1-butyl-3-methylimidazolium hexafluorophosphate (Fluka) and 1 g of molecular sieves 3A (pore size: 3 Ångström; Fluka) was obtained by weighing the individual constituents into a glass beaker.

Example 4

Process According to the Invention Using the Catalyst Composition as Per Example 1

88 g of chlorobenzene were placed in a 300 ml stirring autoclave and 14 g of phenol were dissolved therein. 15 g of the catalyst composition as per Example 1 were added and reacted with a gas mixture containing 97% by volume of carbon monoxide and 3% by volume of oxygen at 15 bar and 90° C. for 250 min. After the reaction was complete, the product is analyzed by gas chromatography (HP 6890 Series, DB-5 (30 m×320 mm×0.25 mm); 50-320° C./14 K/min; FID).

No precipitate of metal salts was observed. A yield of diphenyl carbonate of 8.3% by weight was determined.

Example 5

Process According to the Invention Using the Catalyst Composition as Per Example 2

An experiment analogous to that in Example 4 was carried out using the catalyst composition as per Example 2. No precipitate of metal salts was observed. A yield of diphenyl carbonate of 5.01% by weight was determined.

Example 6

Process According to the Invention Using the Catalyst Composition as Per Example 3

An experiment analogous to that in Example 4 was carried out using 1.5 g of the catalyst composition as per Example 3 in a scaled-down stirring autoclave of otherwise the same construction and initially introducing or dissolving 8.8 g of chlorobenzene and 1.4 g of phenol instead of 88 g of chlorobenzene and 14 g of phenol. The experiment as per Example 3 in combination with Example 6 was accordingly carried out on a scale reduced by a factor of 1/10 compared to the experiments as per Examples 1, 2 in combination with Examples 4, 5. No precipitate of metal salts was observed. A yield of diphenyl carbonate of 1.75% by weight was determined.

Comparative Example 1

Catalyst Composition not According to the Invention

A first catalyst composition which is not according to the invention and is identical to that of Example 3 except that 0.3 g of 1-butyl-3-methylimidazolium tetrafluoroborate (Fluka) were weighed out instead of the mixture of 0.15 g of 1-butyl-3-methylpyrrolidinium tetrafluoroborate (Fluka) and 0.15 g of 1-butyl-3-methyl-imidazolium hexafluorophosphate (Fluka) was produced.

Comparative Example 2

Further Catalyst Composition which is not According to the Invention

A second catalyst composition which is not according to the invention and is identical to that of Example 1 except that 3.0 g of 1-butyl-3-methylimidazolium bromide (Fluka) were weighed out instead of 3.0 g of 1-butyl-3-methylpyrrolidinium trifluoroacetate was produced.

Comparative Example 3

Third Catalyst Composition which is not According to the Invention

A third catalyst composition which is not according to the invention and is identical to that of Example 1 except that 3.0 g of 1-ethyl-3-methylimidazolium bromide (Fluka) were weighed out instead of 3.0 g of 1-butyl-3-methylpyrrolidinium trifluoroacetate was produced.

Comparative Example 4

Fourth Catalyst Composition which is not According to the Invention

A fourth catalyst composition which is not according to the invention and is identical to that of Example 1 except that 3.0 g of trihexyltetradecylphosphonium tetrafluoroborate (Fluka) were weighed out instead of 3.0 g of 1-butyl-3-methylpyrrolidinium trifluoroacetate was produced.

Comparative Example 5

Fifth Catalyst Composition which is not According to the Invention

A fifth catalyst composition which is not according to the invention and is identical to that of Example 1 except that 3.0 g of tetrabutylammonium bromide (Fluka) were weighed out instead of 3.0 g of 1-butyl-3-methylpyrrolidinium trifluoroacetate was produced.

Comparative Example 6

Process Using the Catalyst Composition as Per Comparative Example 1

An experiment analogous to that in Example 6 was carried out using the catalyst composition as per Comparative Example 1. A yield of diphenyl carbonate of 1.89% by weight was determined.

Comparative Example 7

Process Using the Catalyst Composition as Per Comparative Example 2

An experiment analogous to that in Example 4 was carried out using the catalyst composition as per Comparative Example 2. A yield of diphenyl carbonate of 3.89% by weight was determined.

Comparative Example 8

Process Using the Catalyst Composition as Per Comparative Example 3

An experiment analogous to that in Example 4 was carried out using the catalyst composition as per Comparative Example 3. A yield of diphenyl carbonate of 2.44% by weight was determined.

Comparative Example 9

Process Using the Catalyst Composition as Per Comparative Example 4

An experiment analogous to that in Example 4 was carried out using the catalyst composition as per Comparative Example 4. A yield of diphenyl carbonate of 3.69% by weight was determined.

Comparative Example 10

Process Using the Catalyst Composition as Per Comparative Example 5

An experiment analogous to that in Example 4 was carried out using the catalyst composition as per Comparative Example 5. A yield of diphenyl carbonate of 7.5% by weight was determined However, it was found that the palladium catalyst precipitates as black palladium metal.

The invention claimed is:

1. A catalyst composition for preparing diphenyl carbonate which comprises an ionic liquid, wherein the ionic liquid is 1-butyl-3-methylpyrrolidinium trifluoroacetate, 1-butyl-3-methylimidazolium hexafluorophosphate or a mixture thereof and wherein the catalyst composition further comprises a palladium salt, a manganese salt and a base.

2. The catalyst composition as claimed in claim 1, wherein the palladium salt is palladium bromide, palladium acetate or palladium chloride.

3. The catalyst composition as claimed in claim 1, wherein the manganese salt is manganese(II) acetyl acetonate, manganese(III) acetyl acetonate, manganese(II) acetate, manganese(III) acetate or manganese bromide.

4. The catalyst composition as claimed in claim 1, wherein the ionic liquid is 1-butyl-3-methylpyrrolidinium trifluoroacetate or 1-butyl-3-methylimidazolium hexafluorophosphate.

5. The catalyst composition as claimed in claim 1 having from 0.01 to 0.06% by weight of palladium salt, from 0.1 to 0.5% by weight of manganese salt and from 0.5 to 6% by weight of base in the ionic liquid.

6. A process for preparing diphenyl carbonate from a reaction mixture comprising phenol, carbon monoxide and also oxygen and optionally diphenyl carbonate in a reaction zone, wherein the reaction mixture in the reaction zone is passed through a catalyst composition containing an ionic liquid which is 1-butyl-3-methylpyrrolidinium trifluoroacetate or 1-butyl-3-methylimidazolium hexafluorophosphate or a mixture thereof, a palladium salt, a manganese salt and a base.

7. The process as claimed in claim 6, carried out at a temperature of from 75 to 150° C.

8. The process as claimed in claim 6, carried out at a pressure of from 3 to 80 bar.

9. The process of claim 6, wherein the reaction mixture is passed through a separation zone after the reaction zone.

10. The process of claim 7 wherein said temperature is from 85 to 110° C.

11. The process of claim 8, wherein said pressure is from 15 to 30 bar.

* * * * *